(12) United States Patent
Arimoto et al.

(10) Patent No.: US 9,504,249 B2
(45) Date of Patent: Nov. 29, 2016

(54) CONTROL AGENT FOR PLANT PEST AND/OR PLANT DISEASE

(71) Applicant: RIKEN, Wako-shi, Saitama (JP)

(72) Inventors: Yutaka Arimoto, Wako (JP); Takayuki Kashima, Osaka (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 14/434,318

(22) PCT Filed: Oct. 11, 2013

(86) PCT No.: PCT/JP2013/077825
§ 371 (c)(1),
(2) Date: May 7, 2015

(87) PCT Pub. No.: WO2014/058065
PCT Pub. Date: Apr. 17, 2014

(65) Prior Publication Data
US 2015/0313217 A1 Nov. 5, 2015

(30) Foreign Application Priority Data
Oct. 12, 2012 (JP) .................................. 2012-227006

(51) Int. Cl.
*A01N 37/12* (2006.01)

(52) U.S. Cl.
CPC ..................................... *A01N 37/12* (2013.01)

(58) Field of Classification Search
CPC ...................................................... A01N 37/12
See application file for complete search history.

(56) References Cited

U.S. PATENT DOCUMENTS

| 6,277,738 B1 * | 8/2001 | Choi ................. H01L 21/31116 |
| | | 257/E21.252 |
| 6,294,578 B1 | 9/2001 | Arimoto et al. |
| 8,986,722 B2 * | 3/2015 | Suzuki ................... A01N 37/06 |
| | | 424/405 |
| 2001/0034368 A1 | 10/2001 | Arimoto et al. |
| 2003/0008917 A1 | 1/2003 | Brock et al. |
| 2007/0190096 A1 | 8/2007 | Arimoto |
| 2011/0045982 A1 | 2/2011 | Koshio et al. |
| 2012/0316237 A1 | 12/2012 | Suzuki et al. |

FOREIGN PATENT DOCUMENTS

| EP | 2543251 B1 | 5/2015 | |
| JP | 10-251104 A | 9/1998 | |
| JP | 11-029413 A | 2/1999 | |
| JP | 4413444 B2 | 2/2010 | |
| JP | 2013-170146 A | 9/2013 | |
| WO | WO 2011/108220 A1 | 9/2011 | |
| WO | WO 2011108220 A1 * | 9/2011 | ............. A01N 37/06 |

OTHER PUBLICATIONS

Office Action issued by the Moroccan Patent Office in corresponding Moroccan Patent Application on Nov. 16, 2015 (5 pages).
Extended Search Report issued by the European Patent Office in corresponding European Patent Application No. 13845686.8 on Mar. 1, 2016 (5 pages).
International Search Report (PCT/ISA/210) mailed on Jan. 14, 2014, by the Japanese Patent Office as the International Searching Authority for International Application No. PCT/JP2013/077825.
Written Opinion (PCT/ISA/237) mailed on Jan. 14, 2014, by the Japanese Patent Office as the International Searching Authority for International Application No. PCT/JP2013/077825.
Takeda Shokubutu Boueki Sousho, Takeda book series of communicable plant diseases, Takeda Pharmaceutical Company Limited, Feb. 1996. vol. 9.

* cited by examiner

*Primary Examiner* — Yong Chu
(74) *Attorney, Agent, or Firm* — Buchanan Ingersoll & Rooney PC

(57) ABSTRACT

The present invention provides a control agent for a plant pest and/or a plant disease, the control agent being environmentally friendly and having a high control effect. The control agent is a control agent for a plant pest and/or a plant disease, containing a polyglycerin fatty acid ester as an active ingredient. The polyglycerin fatty acid ester is an ester of at least one fatty acid selected from fatty acids having 8 to 10 carbon atoms, and at least one polyglycerin obtained by polymerizing 3 to 10 glycerins.

13 Claims, No Drawings

CONTROL AGENT FOR PLANT PEST AND/OR PLANT DISEASE

TECHNICAL FIELD

The present invention relates to a control agent for plant pests and/or plant diseases.

BACKGROUND ART

Agricultural plants, fruits, vegetables, fruit trees, ornamental plants, and the like are seriously damaged by winged pests such as whiteflies, aphids, and *thrips*. As means for controlling such winged pests, proposed are chemical control, biological control, physical control, and so forth. As chemicals, organophosphates, carbamates, synthetic pyrethroids, and the like are used. However, when chemicals are used, many pests acquire resistance to the chemicals, and eventually the effects are reduced or completely lost in many cases. Moreover, there is a problem that many chemicals have harmful effects on human and animals and hence cannot be used frequently. Some biological and physical controls are also effective but are not fully satisfactory in terms of cost, versatility, and so on under current situations (see Non Patent Literature 1). Accordingly, there is a strong desire for pest controlling means which is inexpensive, highly versatile, and safe for human and animals.

On the other hand, for example, Patent Literature 1 states that, as a plant pest control agent very safe for human and animals, a glycerin fatty acid ester or a polyglycerin fatty acid ester containing a fatty acid having 12 to 18 carbon atoms, such as glycerin monooleate, diglycerin monolaurate, diglycerin oleate, tetraglycerin oleate, hexaglycerin laurate, and decaglycerin laurate, has insecticidal effects against mites and aphids.

Patent Literature 2 describes an insecticide, a miticide, and a microbiocide for plants, which contain one or two or more selected from polyglycerin monofatty acid esters, polyglycerin difatty acid esters, and sorbitol monofatty acid esters as an active ingredient(s).

As described above, an ester compound of a fatty acid having 12 to 18 carbon atoms and monoglycerin or diglycerin is mainly used in conventional insecticides and repellents containing a polyglycerin fatty acid ester as an active ingredient. Nevertheless, from the viewpoints of reducing the cost and the influence on the environment as much as possible, strongly demanded is a versatile control agent effective against various pests/diseases and having higher control effects than the above-described insecticides and repellents.

CITATION LIST

Patent Literatures

Patent Literature 1: Japanese Patent Application Publication No. Hei 10-251104
Patent Literature 2: Japanese Patent Application Publication No. Hei 11-29413

Non Patent Literature

Non Patent Literature 1: "*Takeda shokubutu Boueki Sousho* (Takeda book series of communicable plant diseases), Vol. 9, Recent Topic of New Pests" published by Takeda Pharmaceutical Company Limited on February, 1996

SUMMARY OF INVENTION

Technical Problem

The present invention has been made in view of the above-described points. An object of the present invention is to provide a very safe control agent capable of exhibiting control effects superior to conventional control agents.

Solution to Problem

As a result of intensive studies, the present inventors have found that the use of a chemical containing as an active ingredient an ester compound of a fatty acid having 8 to 10 carbon atoms and polyglycerin obtained by polymerizing 3 to 10 glycerins dramatically improves control effects in comparison with conventional polyglycerin fatty acid ester-based agents. This finding has led to the completion of the present invention.

Specifically, gist of the present invention is as follows.
(1) A control agent for a plant pest and/or a plant disease, comprising a polyglycerin fatty acid ester as an active ingredient, wherein the polyglycerin fatty acid ester is an ester of at least one fatty acid selected from fatty acids having 8 to 10 carbon atoms, and at least one polyglycerin obtained by polymerizing 3 to 10 glycerins.
(2) The control agent according to (1), wherein the polyglycerin contains at least one selected from triglycerin, tetraglycerin, and decaglycerin.
(3) The control agent according to (1) or (2), wherein the plant pest is at least one selected from the group consisting of aphids, whiteflies, mites, *thrips*, and scale insects.
(4) The control agent according to any one of (1) to (3), wherein the plant disease is at least one selected from the group consisting of gray mold and powdery mildew.
(5) The control agent according to any one of (1) to (4), wherein the polyglycerin fatty acid ester has an esterification degree of 20 to 100%.
(6) The control agent according to any one of (1) to (5), wherein the polyglycerin fatty acid ester has an esterification degree of 30 to 80%.
(7) The control agent according to any one of (1) to (6), further comprising a surfactant.
(8) The control agent according to (7), wherein the surfactant includes polyoxyethylene cocoamine.
(9) The control agent according to any one of (1) to (8), further comprising an organic solvent.
(10) The control agent according to any one of (1) to (9), further comprising an oxoacid.
(11) A method for controlling a plant pest and/or a plant disease, comprising spraying a plant with the control agent according to any one of (1) to (10).
(12) The method according to (11), wherein the plant is sprayed with the polyglycerin fatty acid ester at a concentration of 10 mg/dL to 2000 mg/dL.

Advantageous Effects of Invention

The present invention makes it possible to provide a control agent for plant pests and/or plant diseases, the control agent being safe and having higher control effects than conventional control agents.

DESCRIPTION OF EMBODIMENTS

Hereinafter, the present invention will be described in detail.

<<Control Agent for Plant Pest and/or Plant Disease>>

A first embodiment of the present invention is a control agent for plant pests and/or plant diseases and characterized as follows. The control agent contains a polyglycerin fatty acid ester as an active ingredient, and the polyglycerin fatty acid ester is an ester of at least one fatty acid selected from fatty acids having 8 to 10 carbon atoms, and at least one polyglycerin obtained by polymerizing 3 to 10 glycerins.

Note that the term "control" and related terms mean a concept including functioning as a repellent to prevent propagation of plant pests and/or occurrence of diseases in a plant, as well as functioning as an insecticide (including a miticide) against plant pests and a microbiocide (fungicide) against causative microorganisms of plant diseases. Particularly, the control agent of the present invention effectively functions as an insecticide (including a miticide) against a plant pest and as a microbiocide (fungicide) against causative microorganisms of plant diseases.

<Polyglycerin Fatty Acid Ester>

In Description and Claims, the term polyglycerin fatty acid ester means a compound in which two or more glycerins polymerize to form polyglycerin, and a part or all of hydroxyl groups contained in the polyglycerin form an ester bond (s) with a fatty acid.

The polyglycerin fatty acid ester contained as an active ingredient in the control agent for plant pests and/or plant diseases of the present invention is a polyglycerin fatty acid ester in which at least one polyglycerin having a degree of polymerization of 3 to 10 forms an ester bond with at least one fatty acid having 8 to 10 carbon atoms. The polyglycerin having a degree of polymerization of 3 to 10 includes triglycerin, tetraglycerin, pentaglycerin, hexaglycerin, heptaglycerin, octaglycerin, nonaglycerin, and decaglycerin.

Among these, at least one selected from the group consisting of triglycerin, tetraglycerin, and decaglycerin is preferable.

Moreover, the fatty acid having 8 to 10 carbon atoms is preferably one or more selected from caprylic acid and capric acid.

In Description and Claims, the term "esterification degree" is an index showing, in terms of average (%), how many hydroxyl groups among all hydroxyl groups (the number) contained in polyglycerin constituting a polyglycerin fatty acid ester form ester bonds with a carboxyl group of a fatty acid.

In the present invention, the esterification degree is preferably 20 to 100%, more preferably 30 to 80%, furthermore preferably 30 to 60%, and particularly preferably 30 to 50%.

When the esterification degree is within the above-described range, excellent control effects can be obtained against various pests and diseases.

A commercially-available product may be employed as the polyglycerin fatty acid ester used in the present invention, or the polyglycerin fatty acid ester may be synthesized by a known method.

For the synthesis, the method for synthesizing the polyglycerin fatty acid ester is not particularly limited. For example, reference can be made to the synthesis method described in Japanese Patent No. 4413444.

One polyglycerin fatty acid ester may be used alone, or two or more polyglycerin fatty acid esters may be used in combination.

Further, in the case where two or more polyglycerin fatty acid esters are combined, among all the polyglycerin fatty acid esters, a ratio of the polyglycerin fatty acid ester obtained by forming an ester bond between the polyglycerin having a degree of polymerization of 3 to 10 and the fatty acid having 8 to 10 carbon atoms is preferably 30 to 100 mass %, more preferably 50 to 100 mass %, furthermore preferably 80 to 100 mass %, and particularly preferably 90 to 100 mass %. The ratio may be 100 mass %.

The control agent of the present invention is stored as an original solution in a concentrated form, and can be diluted with water when used. Thus, the concentration of the polyglycerin fatty acid ester in the control agent during the storage is not particularly limited, and should be set as appropriate depending on the situation. When the control agent of the present invention is diluted with water and used, the polyglycerin fatty acid ester in the diluted liquid preferably has a concentration of 10 mg/dL to 2000 mg/dL, more preferably has a concentration of 20 to 1000 mg/dL, and particularly preferably 50 to 500 mg/dL.

<Surfactant>

The control agent of the present invention may contain a surfactant as an auxiliary agent, besides the polyglycerin fatty acid ester. Adding a surfactant makes the active ingredient in the spray solution readily adhere to pests or mites and cover surfaces thereof, hence increasing the physical action such as blocking the spiracles. Further, against fungi also, the active ingredient adheres to surfaces of hyphae or spores in the same manner, hence suppressing the activities.

Nonionic surfactants include polyoxyethylene alkyl ethers, polyoxyethylene castor oils, polyoxyethylene sorbitan fatty acid esters, and polyoxyethylene alkylphenyl ethers. Polyoxyethylene alkyl ethers, polyoxyethylene castor oils, and polyoxyethylene sorbitan fatty acid esters (particularly, polyoxyethylene sorbitan monolaurate) are preferably used.

Amphoteric surfactants include polyoctyl aminoethyl glycine, coconut oil fatty acid amidopropyl betaine, imidazoline derivatives, and the like. Above all, polyoctyl aminoethyl glycine and coconut oil fatty acid amidopropyl betaine are preferably used.

Cationic surfactants include polyoxyethylene cocoamine, lauryl dihydroxyethylamine, cationized cellulose, laurylt-rimethylammonium chloride, quaternary ammonium salts, stearyltrimethylammonium chloride, and the like. Above all, polyoxyethylene cocoamine, cationized cellulose, and lauryl dihydroxyethylamine are preferably used.

Anionic surfactants include potash soap, sodium lauryl sulfate, sodium polyoxyethylene lauryl sulfate, sodium polyoxyethylene alkyl ether sulfate, castor oil sodium sulfate, and alkyl ether phosphate esters. Above all, potash soap, sodium lauryl sulfate, and castor oil sodium sulfate are preferably used.

Among these, nonionic surfactants and cationic surfactants are preferable. Polyoxyethylene alkyl ethers (preferably alkyl groups having 12 to 26 carbon atoms, more preferably alkyl groups having 12 to 18 carbon atoms), polyoxyethylene sorbitan monolaurate, lauryl dihydroxyethylamine, and polyoxyethylene cocoamine are more preferable, and polyoxyethylene cocoamine is particularly preferable.

One of the surfactants may be used alone, or two or more of the surfactants may be used in combination.

In the case of using such a surfactant, the surfactant is preferably added at a ratio of 0.01 to 10 parts by mass, and more preferably 0.1 to 5 parts by mass, relative to 100 parts by mass of the polyglycerin fatty acid ester. When the ratio is within the above-described range, the advantages of using the surfactant can be sufficiently exhibited.

<Organic Solvent>

The control agent of the present invention may contain an organic solvent. If a polyglycerin fatty acid ester is left standing in a cool dark place, portions thereof aggregate into a cotton-like form and precipitate as time elapses in some cases. Nevertheless, adding an organic solvent makes it possible to reduce the aggregation and precipitation.

The organic solvent includes acetone, isobutyl alcohol, isopropyl alcohol, isopentyl alcohol, ethyl ether, ethyl alcohol, xylene, cresols, cyclohexane, isobutyl acetate, ethyl acetate, chloroform, normal hexane, normal propyl alcohol, methanol, and the like. Above all, acetone, ethyl alcohol, cyclohexane, normal hexane, and methanol are preferable; ethyl alcohol, normal hexane, and methanol are more preferable; and ethyl alcohol and normal hexane are furthermore preferable.

In the case of adding such an organic solvent, the organic solvent is preferably added at a ratio of 0.01 to 30 parts by mass, and more preferably 0.1 to 10 parts by mass, relative to 100 parts by mass of the polyglycerin fatty acid ester. When the ratio is within the above-described range, the advantages of using the organic solvent can be sufficiently exhibited.

<Oxoacid>

The control agent of the present invention may contain an oxoacid. If a polyglycerin fatty acid ester is left standing in a room or a cool dark place, portions thereof aggregate into a cotton-like form and precipitate as time elapses in some cases. Nevertheless, adding an oxoacid makes it possible to reduce the aggregation and precipitation.

The oxoacid includes boric acid, carboxylic acids, nitric acid, phosphorous acid, phosphoric acid, sulfurous acid, sulfuric acid, acetic acid, propionic acid, butyric acid, valeric acid, lactic acid, sulfonic acids, and the like. Above all, phosphorous acid, phosphoric acid, lactic acid, and acetic acid are preferably; phosphoric acid, lactic acid, and acetic acid are more preferably.

In the case of adding such an oxoacid, the oxoacid is preferably added at a ratio of 0.01 to 30 parts by mass, and more preferably 0.1 to 10 parts by mass, relative to 100 parts by mass of the polyglycerin fatty acid ester. When the ratio is within the above-described range, the advantages of using the oxoacid can be sufficiently exhibited.

<Other Ingredients>

To the control agent of the present invention, a known adjuvant/additive normally used in agricultural chemical compositions may be added as necessary besides the above-described ingredients, as long as the effects of the control agent of the present invention are not interrupted. Examples of such an adjuvant/additive include a carrier, an antioxidant, a dispersant, a preservative, a synergist, an emulsifier, a suspension, a sticker, a wetting agent, a penetrant, a mucilage, a stabilizer, an adhesive, an adsorbent, and the like.

Further, the control agent of the present invention may be mixed as appropriate with another agricultural chemical and used in combination, as long as the effects of the control agent of the present invention are not interrupted. Examples of the agricultural chemical include a microbiocide, an insecticide, a plant growth control agent, a herbicide, and the like.

<Pest and Disease>

A target plant pest includes aphids, whiteflies, mites, *thrips*, and scale insects. Above all, the control agent of the present invention exhibits excellent control effects against aphids, whiteflies, and spider mites. Specific examples of aphids, whiteflies, mites, *thrips*, and scale insects include the following.

[Mites (Acarina)]
(Tarsonemidae)
 broad mite (*Polyphagotarsonemus latus*),
 cyclamen mite (*Steneotarsonemau pallidus*),
 tarsonemid mites (*Tarsonemus bilobatus, Tarsonemus confuses, Tarsonemus waitei*), and the like.
(Pyemotidae)
 itch mite (*Pyemotes ventricosus*), and the like.
(Eupodidae)
 earth mite (*Penthaleus major*), and the like.
(Tenuipalpidae)
 false spider mite (*Brevipalpus californicus*),
 citrus flat mite (*Brevipalpus lewisi*),
 scarlet tea mite (*Brevipalpus obovatus*),
 cactus flat mite (*Brevipalpus russulus*),
 pineapple false spider mite (*Dolichotetranychus floridanus*),
 phalaenopsis mite (*Tenuipalpus pacificus*),
 persimmon false spider mite (*Tenuipalpus zhizhilashviliae*), and the like.
(Tuckerellidae)
 peacock mite (*Tuckerella pavoniformis*), and the like.
(Tetranychidae)
 clover mite (*Bryobia praetiosa*),
 brown mite (*Bryobia rubrioculus*),
 apricot spider mite (*Eotetranychus boreus*),
 spider mite (*Eotetranychus geniculatus*),
 apple yellow mite (*Eotetranychus pruni*),
 six-spotted spider mite (*Eotetranychus sexmanaculatus*),
 Smith spider mite (*Eotetranychus smithi*),
 Garman spider mite (*Eotetranychus uncatus*),
 tea red spider mite (*Oligonychus coffeae*),
 sugi spider mite (*Oligonychus hondoensis*),
 southern red mite (*Oligonychus ilicis*),
 larch red mite (*Oligonychus karamatus*),
 sugarcane spider mite (*Oligonychus orthius*),
 citrus red mite (*Panonychus citri*),
 European red mite (*Panonychus ulmi*),
 carmine spider mite (*Tetranychus cinnabarinus*),
 sweet potato/tomato red spider mite (*Tetranychus evansi*),
 Kanzawa spider mite (*Tetranychus kanzawai*),
 two-spotted spider mite (*Tetranychus urticae*),
 sweet cherry spider mite (*Tetranychus viennensis*), and the like.
(Eriophidae)
 Pink tea mite (*Acaphylla theae*),
 fig mite (*Aceria ficus*),
 litchi mite (*Aceria* litchi),
 carnation bud mite (*Aceria paradianthi*),
 wheat curl mite (*Aceria tulipae*),
 tomato russet mite (*Aculops lycopersici*),
 pink citrus rust mite (*Aculops* pelekassi),
 pulm rust mite (*Aculus fockeui*),
 apple rust mite (*Aculus schlechtendali*),
 purple tea mite (*Calacarus carinatus*),
 leaf coating mite (*Cisaberoptus kenyae*),
 grape erineum mite (*Colomerus vitis*),
 purple tea mite (*Calacarus carinatus*),
 grape leaf rust mite (*Calepitrimerus vitis*),
 pear rust mite (*Epitrimerus pyri*),
 Japanese pear rust mite (*Eriophyes chibaensis*), and the like,
 *chrysanthemum* rust mite (*Paraphytoptus kikus*).
(Acaridae)
 flour mite (*Acarus siro*),
 brown-legged mite (*Aleuroglyphus ovatus*),
 bulb mite (*Rhizoglyphus robini*),
 cereal mite (*Tyrophagus putrescentiae*), and the like.

[*Thrips* (Thysanoptera)]
(Thripidae)
grass thrip (*Anaphothrips obscurus*),
timothy thrip (*Chirothrips manicatus*),
bean flower thrip (*Megaleurothrips distalis*),
tea thrip (*Dendrothrips minowai*),
eastern flower thrip (*Frankliniella intonsa*),
lily yellow thrip (*Frankliniella lilivora*),
greenhouse thrip (*Heliothrips haemorrhoidalis*),
composite thrip (*Microcephalothrips abdominalis*),
soybean thrip (*Mycterothrips glycines*),
mulberry thrip (*Pseudodendrothrips mori*),
yellow tea thrip (*Scirtothrips dorsalis*),
red-banded thrip (*Selenothrips rubrocinctus*),
rice thrip (*Stenchaetothrips biformis*),
onion thrip (*Thrips alliorum*),
loquat thrip (*Thrips coloratus*),
honeysuckle thrip (*Thrips flavas*),
flower-dwelling thrip (*Thrips hawaiiensis*),
*chrysanthemum* thrip (*Thrips nigropilosus*),
melon thrip (*Thrips palmi*),
western flower thrip (*Frankliniella occidentalis*),
Japanese flower thrip (*Thrips setosus*),
gladiolus thrip (*Thrips simplex*), and the like.
(Phlaeothripidae)
grass thrip (*Haplothrips aculeatus*),
Chinese thrip (*Haplothrips chinensis*),
predatory *thrips* (*Haplothrips kurdjumovi*),
red clover thrip (*Haplothrips nigar*),
*Leeuwania pasanii*,
camphor thrip (*Liothrips flordensis*),
lily thrip (*Liothrips vaneeckei*),
*Litotetothrips pasaniae*,
Japanese gall-forming thrip (*Ponticulothrips diospyrosi*), and the like.
[Whiteflies]
(Aleyrodidae)
orange spiny whitefly (*Aleurocanthus spiniferus*),
grape whitefly (*Aleurolobus taonabae*),
grape whitefly (*Aleurolobus taonabae*),
Japanese laurel whitefly (*Aleurotuberculatus aucubae*),
*camellia* spiny whitefly (*Aleurocanthus camelliae*),
sweet potato whitefly (*Bemisia tabaci*),
citrus whitefly (*Dialeurodes citri*),
strawberry whitefly (*Trialeurodes packardi*),
greenhouse whitefly (*Trialeurodes vaporariorum*), and the like.
[Aphids]
(Phylloxeridae)
grape root aphid (*Viteus vitifolii*), and the like.
(Pemphigidae)
apple root aphid (*Aphidonuguis mali*),
wooly apple aphid (*Eriosoma lanigerum*),
sugarcane root aphid (*Geoica lucifuga*), and the like.
(Aphididae)
pea aphid (*Acyrthosiphon pisum*),
spirea aphid (*Aphis citricola*),
cowpea aphid (*Aphis craccivora*),
willow aphid (*Aphis farinose yanagicola*),
strawberry root aphid (*Aphis forbesi*),
soybean aphid (*Aphis glycines*),
cotton aphid (*Aphis gossypii*),
leafcurl plum aphid (*Brachycaudus helichrysi*),
cabbage aphid (*Brevicoryne brassicae*),
tulip bulb aphid (*Dysaphis tulipae*),
woolly apple aphid (*Eriosoma lanigerum*),
European birch aphid (*Euceraphis punctipennis*),
mealy plum aphid (*Hyalopterus pruni*),
mustard aphid (*Lipaphis erysimi*),
*chrysanthemum* aphid (*Macrosiphoniella sanborni*),
potato aphid (*Macrosiphum euphorbiae*),
bean aphid (*Megoura crassicauda*),
pear aphid (*Melanaphis siphonella*),
apple leaf-curling aphid (*Myzus malisuctus*),
plum aphid (*Myzus mumecola*),
green peach aphid (*Myzus persicae*),
currant-lettuce aphid (*Nasonovia ribisnigri*),
onion aphid (*Neotoxoptera formosana*),
apple aphid (*Ovatus malicolens*),
waterlily aphid (*Rhopalosophum nymphaeae*),
corn lead aphid (*Rhopalosiphum maidis*),
wheat aphid (*Rhopalosophum padi*),
rice root aphid (*Rhopalosophum rufiabdominalis*),
wormwood root aphid (*Sappaphis piri*),
pear aphid (*Schizaphis piricola*),
celery aphid (*Semiaphis heraclei*),
wheat aphid (*Sitobion akebiae*),
rose aphid (*Sitobion ibarae*),
*camellia* aphid (*Toxoptera aurantii*),
black citrus aphid (*Toxoptera citricidus*),
peach aphid (*Tuberocephalus momonis*),
Taiwan aphid (*Uroeucon formosanum*), and the like,
safflower aphid (*Uroleucon gobonis*),
azalea aphid (*Vesiculaphis caricis*).
[Scale Insects]
(Margarodidae)
giant mealybug (*Drosicha corpulenta*),
cottony cushion scale (*Icerya purchasi*), and the like.
(Pseudococcidae)
Matsumoto mealybug (*Crisicoccus matsumotoi*),
pine mealybug (*Crisicoccus pini*),
pineapple mealybug (*Dysmicoccus brevipes*),
pear mealybug (*Dysmicoccus wistariae*),
azalea mealybug (*Phenacoccus azalea*),
citrus mealybug (*Planococcus citri*),
Japanese mealybug (*Planococcus kraunhiae*),
citrus mealybug (*Pseudococcus citriculus*),
comstock mealybug (*Pseudococcus comstocki*), and the like.
(Coccidae)
Indian wax scale (*Ceroplastes ceriferus*),
tortoise wax scale (*Ceroplastes japonicas*),
pink wax scale (*Ceroplastes rubens*),
soft scale (*Coccus discrepans*),
brown soft scale (*Coccus hesperidum*),
citricola scale (*Coccus pseudomagnoliarum*),
Chinese white-wax scale (*Ericerus pela*),
kuno scale (*Eulecanium kunoense*),
European fruit scale (*Lecanium corni*),
grapevine scale (*Lecanium persicae*),
citrus soft scale (*Pulvinaria aurantii*),
citrus cottony scale (*Pulvinaria citricola*),
Japanese soft scale (*Pulvinaria horii*),
cottony mulberry scale (*Pulvinaria kuwacola*), and the like.
(Diaspididae)
citrus scale (*Andaspis kashicola*),
California red scale (*Aonidiella aurantii*),
citrus yellow scale (*Aonidiella citrine*),
coconut scale (*Aspidiotus destructor*),
oleander scale (*Aspidiotus hederae*),
Florida red scale (*Chrysomphalus ficus*),
San Jose scale (*Comstockaspis perniciosa*),
*camellia* mining scale (*Duplaspidiotus claviger*), purple scale (*Lepidosaphes beckii*),
oystershell scale (*Lepidosaphes ulmi*),
pear scale (*Lepholeucaspis japonica*),
brown pineapple scale (*Melanaspis bromiliae*),
pear scale (*Parlatoreopsis pyri*),
armored scale (*Parlatoria camelliae*),
tea black scale (*Parlatoria theae*),
black *parlatoria* scale (*Parlatoria ziziphi*),
fern scale (*Pinnaspis aspidistrae*),
camphor scale (*Pseudaonidia duplex*),
peony scale (*Pseudaonidia paeoniae*),
white *prunicola* scale (*Pseudaulacaspis prunicola*),
arrowhead scale (*Unaspis yanonensis*), and the like.

The plant disease includes gray mold, powdery mildew, and the like. Specifically, the control agent of the present invention exhibits excellent control effect against causative microorganisms of gray mold, such as *Botrytis* species, and pathogens of powdery mildew, such as *Erysiphe necator* or *Uncinula necator* (grape (*Vitis*)), *Blumeria graminis* (wheat-like cereals (Poaceae)), *Sphaerotheca pannosa* (peach (*Prunus persica*)), *Sphaerotheca humuli* (strawberry (*Fragaria×ananassa*)), *Oidium lycopersici* (tomato (*Solanum lycopersicum*)), *Erysiphe polygoni* and *Sphaerotheca cucurbitae* (cucumber (*Cucumis sativus*)) *Sphaerotheca pannosa* and *Uncinula simulans* (rose (*Rosa*)), *Phyllactinia moricola* (mulberry (*Morus*)), and the like.

<Target Plant>

Additionally, a target plant to be sprayed with the control agent of the present invention is not particularly limited, as long as the pests can grow in the plant or the diseases can occur in the plant. Examples thereof include cucumber, strawberry, tomato, eggplant (*Solanum melongena*), bell pepper (*Capsicum annuum*), grape, citrus fruits (Citreae), apple (*Malus domestica*), peach, wheat-like cereals, rose, mulberry, kidney bean (*Phaseolus vulgaris*), white radish (*Raphanus sativus* var. *longipinnatus*), cabbage (*Brassica oleracea* var. *capitata*), *Camellia sasanqua*, *Petunia*, and the like.

<<Method for Controlling Plant Pest and/or Plant Disease>>

A second embodiment of the present invention is a method for controlling plant pests and/or plant diseases, including spraying the above-described control agent on a plant having a plant pest and/or a plant disease.

The control agent is preferably sprayed on a plant in such a manner that the plant is sprayed with the polyglycerin fatty acid ester at a concentration of 10 mg/dL to 2000 mg/dL, more preferably at a concentration of 20 to 1000 mg/dL, and particularly preferably 50 to 500 mg/dL. In a case where the original solution of the control agent is diluted, the polyglycerin fatty acid ester should be diluted to be within the above-described range using water.

Moreover, when the diluted control agent is sprayed on a plant, the polyglycerin fatty acid ester is preferably sprayed in an amount of 0.1 to 100 kg per ha, more preferably sprayed in an amount of 0.5 to 30 kg per ha, and furthermore preferably 1 to 3 kg per ha.

The spraying timing may be at the time when or before a plant pest and/or a plant disease are present on a plant. Nevertheless, the spraying timing is preferably at the time when a plant pest and/or a plant disease are present on a plant because remarkable insecticidal/miticidal/microbiocidal (fungicidal) effects are exhibited.

The agent may be sprayed on the entire plant in which a plant pest and/or a plant disease are present or may occur. Alternatively, the agent may be sprayed directly on a part of of a plant where a plant pest and/or a plant disease are present.

The number of times of the spraying may be only one, or the agent may be sprayed two times or more.

EXAMPLES

Next, the control effects of the control agent of the present invention will be specifically illustrated based on Examples. However, the present invention is not limited to these examples.

The abbreviations in each table are as follows.
C8: caprylic acid
C10: capric acid
C12: lauric acid
C18-1: oleic acid
C18-2: linoleic acid "Tri- and tetraglycerins" means a mixture of triglycerin and tetraglycerin (1:1) (mass ratio).

Moreover, in each table, for example, a polyglycerin fatty acid ester with triglycerin and C8 and an esterification degree of 40% means that approximately 40% of hydroxyl groups among all hydroxyl groups in the triglycerin form ester bonds with caprylic acid on average.

Example 1

Test chemicals were each prepared by mixing one polyglycerin fatty acid ester (active ingredient) shown in Table 1 with polyoxyethylene cocoamine (product name: SORPOL 7643 (manufactured by TOHO CHEMICAL INDUSTRY Co., Ltd.)) at (99:1) (mass ratio) (approximately 1 parts by mass of polyoxyethylene cocoamine relative to 100 parts by mass of the polyglycerin fatty acid ester).

Likewise, test chemicals were each prepared by mixing one compound shown in Table 2 with polyoxyethylene cocoamine (product name: SORPOL 7643 (manufactured by TOHO CHEMICAL INDUSTRY Co., Ltd.)) at 99:1 (mass ratio).

Approximately 200 two-spotted spider mites per leaf were released to kidney bean seedlings, and cultured in a greenhouse for 3 days, allowing the mites to lay eggs. Then, one of the test chemicals in Tables 1 and 2 having been diluted with water to a predetermined concentration (100 mg/dl) was sprayed thereon using a sprayer. The plants were further grown in the greenhouse, and the number of the adults was counted 2 weeks thereafter. Meanwhile, the number of adults in an untreated plot was counted, as well, in the same manner. A mortality of the two-spotted spider mites was calculated by the following equation, and a miticidal effect was determined according to the following evaluation criteria. Tables 1 and 2 show the result.

(Mortality of Two-Spotted Spider Mites)

> Mortality of two-spotted spider mites={1−(the number of adults in a plot treated with a test chemical after 2 weeks from the spraying)/(the number of adults in the untreated plot)}×100

(Evaluation Criteria)
A: the mortality of the two-spotted spider mites was 95% or more
B: the mortality of the two-spotted spider mites was 80% or more but less than 95%
C: the mortality of the two-spotted spider mites was 60% or more but less than 80%
D: the mortality of the two-spotted spider mites was less than 60%

TABLE 1

| Fatty acid | C8 | C8 | C8 | C10 | C10 | C10 | C12 | C12 | C18-1 | C18-1 |
|---|---|---|---|---|---|---|---|---|---|---|
| Esterification degree (%) | 40 | 50 | 100 | 40 | 50 | 100 | 40 | 50 | 40 | 50 |
| Monoglycerin | — | — | D | — | — | D | D | D | D | D |
| Diglycerin | C | C | D | C | C | D | D | D | D | D |
| Triglycerin | A | A | B | A | A | B | C | C | D | D |
| Tri- and tetraglycerins | A | A | B | A | A | B | C | C | D | D |
| Decaglycerin | A | A | B | A | A | B | C | C | D | D |

TABLE 2

| | C8 | C10 | C12 | C14 | C16 | C18-1 | C18-2 |
|---|---|---|---|---|---|---|---|
| Monoglycerin monofatty acid ester | D | D | D | D | D | D | D |
| Monoglycerin diaceto monofatty acid ester | D | D | D | — | — | D | — |
| Glycerin citric and fatty acid ester | — | — | D | — | — | D | — |
| Sorbitan fatty acid ester | — | — | D | — | — | D | — |
| Propylene glycol fatty acid ester | — | — | D | — | — | D | — |

<Result>

The compositions of the present invention using as an active ingredient an ester of polyglycerin obtained by polymerizing 3 to 10 glycerins and a fatty acid having 8 to 10 carbon atoms caused a high mortality of the two-spotted spider mites in comparison with compositions using as an active ingredient a fatty acid ester of monoglycerin or diglycerin, and compositions using as an active ingredient an ester of glycerin and a fatty acid having 12 to 18 carbon atoms.

Moreover, the compositions of the present invention caused a high mortality of the two-spotted spider mites in comparison with compositions using as an active ingredient a compound other than the glycerin fatty acid ester (monoglycerin diaceto monofatty acid ester, glycerin citric and fatty acid ester, sorbitan fatty acid ester, propylene glycol fatty acid ester).

Example 2

Test chemicals were each prepared by mixing one polyglycerin fatty acid ester (active ingredient) shown in Table 3 with polyoxyethylene cocoamine (product name: SORPOL 7643 (manufactured by TOHO CHEMICAL INDUSTRY Co., Ltd.)) at (99:1) (mass ratio) (approximately 1 parts by mass of polyoxyethylene cocoamine relative to 100 parts by mass of the polyglycerin fatty acid ester).

Likewise, test chemicals were each prepared by mixing one compound shown in Table 4 with polyoxyethylene cocoamine (product name: SORPOL 7643 (manufactured by TOHO CHEMICAL INDUSTRY Co., Ltd.)) at 99:1 (mass ratio).

Approximately 200 Kanzawa spider mites per leaf were released to kidney bean seedlings, and cultured in a greenhouse for 3 days, allowing the mites to lay eggs. Then, one of the test chemicals in Tables 3 and 4 having been diluted with water to a predetermined concentration (100 mg/dl) was sprayed thereon using a sprayer. The plants were further grown in the greenhouse, and the number of the adults was counted 2 weeks thereafter. Meanwhile, the number of adults in an untreated plot was counted, as well, in the same manner. A mortality of the mites was calculated by the following equation, and an anti-Kanzawa spider mite effect was determined according to the following evaluation criteria. Tables 3 and 4 show the result.

(Mortality of Kanzawa Spider Mites)

Mortality of Kanzawa spider mites={1−(the number of adults in a plot treated with a test chemical after 2 weeks from the spraying)/(the number of adults in the untreated plot)}×100

(Evaluation Criteria)
A: the mortality of the Kanzawa spider mites was 95% or more
B: the mortality of the Kanzawa spider mites was 80% or more but less than 95%
C: the mortality of the Kanzawa spider mites was 60% or more but less than 80%
D: the mortality of the Kanzawa spider mites was less than 60%

TABLE 3

| Fatty acid | C8 | C8 | C8 | C10 | C10 | C10 | C12 | C12 | C18-1 | C18-1 |
|---|---|---|---|---|---|---|---|---|---|---|
| Esterification degree (%) | 40 | 50 | 100 | 40 | 50 | 100 | 40 | 50 | 40 | 50 |
| Monoglycerin | — | — | D | — | — | D | D | D | D | D |
| Diglycerin | C | C | D | C | C | D | D | D | D | D |
| Triglycerin | A | A | B | A | A | B | C | C | D | D |
| Tri- and tetraglycerins | A | A | B | A | A | B | C | C | D | D |
| Decaglycerin | A | A | B | A | A | B | C | C | D | D |

TABLE 4

|  | C8 | C10 | C12 | C14 | C16 | C18-1 | C18-2 |
|---|---|---|---|---|---|---|---|
| Monoglycerin monofatty acid ester | D | D | D | D | D | D | D |
| Monoglycerin diaceto monofatty acid ester | D | D | D | — | — | D | — |
| Glycerin citric and fatty acid ester | — | — | D | — | — | D | — |
| Sorbitan fatty acid ester | — | — | D | — | — | D | — |
| Propylene glycol fatty acid ester | — | — | D | — | — | D | — |

<Result>

The compositions of the present invention using as an active ingredient an ester of polyglycerin obtained by polymerizing 3 to 10 glycerins and a fatty acid having 8 to 10 carbon atoms caused a high mortality of the Kanzawa spider mites in comparison with compositions using as an active ingredient a fatty acid ester of monoglycerin or diglycerin, and compositions using as an active ingredient an ester of glycerin and a fatty acid having 12 to 18 carbon atoms.

Moreover, the compositions of the present invention caused a high mortality of the two-spotted spider mites in comparison with compositions using as an active ingredient a compound other than the glycerin fatty acid ester (monoglycerin diaceto monofatty acid ester, glycerin citric and fatty acid ester, sorbitan fatty acid ester, propylene glycol fatty acid ester).

Example 3

Test chemicals were each prepared by mixing one polyglycerin fatty acid ester (active ingredient) shown in Table 5 with polyoxyethylene cocoamine (product name: SORPOL 7643 (manufactured by TOHO CHEMICAL INDUSTRY Co., Ltd.)) at (99:1) (mass ratio) (approximately 1 parts by mass of polyoxyethylene cocoamine relative to 100 parts by mass of the polyglycerin fatty acid ester).

Likewise, test chemicals were each prepared by mixing one compound shown in Table 6 with polyoxyethylene cocoamine (product name: SORPOL 7643 (manufactured by TOHO CHEMICAL INDUSTRY Co., Ltd.)) at 99:1 (mass ratio).

Cotton aphids were grown on white radish seedlings, and the number of the aphids was counted. One of the test chemicals in Tables 5 and 6 having been diluted with water to a predetermined concentration (100 mg/dl) was sprayed thereon using a sprayer. The plants were further grown in a greenhouse, and the number of the aphids alive was counted 1 week thereafter. A mortality of the aphids was calculated from the number of the aphids before the treatment and the number of the aphids after the treatment by the following equation, and an aphicidal effect was determined according to the following evaluation criteria. Tables 5 and 6 show the result.

(Mortality of Aphids)

Mortality of aphids={1−(the number of adults after 1 week from the spraying of a test chemical)/(the number of adults before the spraying)}×100

(Evaluation Criteria)

A: the mortality of the aphids was 95% or more
B: the mortality of the aphids was 80% or more but less than 95%
C: the mortality of the aphids was 60% or more but less than 80%
D: the mortality of the aphids was less than 60%

TABLE 5

| Fatty acid | C8 | C8 | C8 | C10 | C10 | C10 | C12 | C12 | C18-1 | C18-1 |
|---|---|---|---|---|---|---|---|---|---|---|
| Esterification degree (%) | 40 | 50 | 100 | 40 | 50 | 100 | 40 | 50 | 40 | 50 |
| Monoglycerin | — | — | D | — | — | D | D | D | D | D |
| Diglycerin | C | C | D | C | C | D | D | D | D | D |
| Triglycerin | A | A | B | A | A | B | C | C | D | D |
| Tri- and tetraglycerins | A | A | B | A | A | B | C | C | D | D |
| Decaglycerin | A | A | B | A | A | B | C | C | D | D |

TABLE 6

|  | C8 | C10 | C12 | C14 | C16 | C18-1 | C18-2 |
|---|---|---|---|---|---|---|---|
| Monoglycerin monofatty acid ester | D | D | D | D | D | D | D |
| Monoglycerin diaceto monofatty acid ester | D | D | D | — | — | D | — |
| Glycerin citric and fatty acid ester | — | — | D | — | — | D | — |
| Sorbitan fatty acid ester | — | — | D | — | — | D | — |
| Propylene glycol fatty acid ester | — | — | D | — | — | D | — |

<Result>

The compositions of the present invention using as an active ingredient an ester of polyglycerin obtained by polymerizing 3 to 10 glycerins and a fatty acid having 8 to 10 carbon atoms caused a high mortality of the cotton aphids in comparison with compositions using as an active ingredient a fatty acid ester of monoglycerin or diglycerin, and compositions using as an active ingredient an ester of glycerin and a fatty acid having 12 to 18 carbon atoms.

Moreover, the compositions of the present invention caused a high mortality of the two-spotted spider mites in comparison with compositions using as an active ingredient a compound other than the glycerin fatty acid ester (monoglycerin diaceto monofatty acid ester, glycerin citric and fatty acid ester, sorbitan fatty acid ester, propylene glycol fatty acid ester).

Example 4

Test chemicals were each prepared by mixing one polyglycerin fatty acid ester (active ingredient) shown in Table 7 with polyoxyethylene cocoamine (product name: SORPOL 7643 (manufactured by TOHO CHEMICAL INDUSTRY Co., Ltd.)) at (99:1) (mass ratio) (approximately 1 parts by mass of polyoxyethylene cocoamine relative to 100 parts by mass of the polyglycerin fatty acid ester).

Likewise, test chemicals were each prepared by mixing one compound shown in Table 8 with polyoxyethylene cocoamine (product name: SORPOL 7643 (manufactured by TOHO CHEMICAL INDUSTRY Co., Ltd.)) at 99:1 (mass ratio).

Adult sweet potato whiteflies were released to kidney bean seedlings for 3 days, and allowed to lay eggs. Then, the adults were removed, while the remaining whiteflies were cultured in a greenhouse, and the number of the third-stage nymphs was counted. Subsequently, one of the test chemicals in Tables 7 and 8 having been diluted with water to a predetermined concentration (100 mg/dl) was sprayed thereon using a sprayer. The plants were further grown in the greenhouse, and the number of newly-emerged adults was counted. A mortality of the sweet potato whiteflies was calculated from the number before the treatment and the number of the newly emerged whiteflies by the following equation, and an anti-sweet potato whitefly effect was determined according to the following evaluation criteria. Tables 7 and 8 show the result.

(Mortality of Sweet Potato Whiteflies)

Mortality of sweet potato whiteflies={1−(the number of newly-emerged sweet potato whiteflies after the spraying of a test chemical)/(the number of third-stage nymphs before the spraying)}×100

(Evaluation Criteria)
A: the mortality of the sweet potato whiteflies was 95% or more
B: the mortality of the sweet potato whiteflies was 80% or more but less than 95%
C: the mortality of the sweet potato whiteflies was 60% or more but less than 80%
D: the mortality of the sweet potato whiteflies was less than 60%

TABLE 7

| Fatty acid | C8 | C8 | C8 | C10 | C10 | C10 | C12 | C12 | C18-1 | C18-1 |
|---|---|---|---|---|---|---|---|---|---|---|
| Esterification degree (%) | 40 | 50 | 100 | 40 | 50 | 100 | 40 | 50 | 40 | 50 |
| Monoglycerin | — | — | D | — | — | D | D | D | D | D |
| Diglycerin | C | C | D | C | C | D | D | D | D | D |
| Triglycerin | A | A | B | A | A | B | C | C | D | D |
| Tri- and tetraglycerins | A | A | B | A | A | B | C | C | D | D |
| Decaglycerin | A | A | B | A | A | B | C | C | D | D |

TABLE 8

|  | C8 | C10 | C12 | C14 | C16 | C18-1 | C18-2 |
|---|---|---|---|---|---|---|---|
| Monoglycerin monofatty acid ester | D | D | D | D | D | D | D |
| Monoglycerin diaceto monofatty acid ester | D | D | D | — | — | D | — |
| Glycerin citric and fatty acid ester | — | — | D | — | — | D | — |
| Sorbitan fatty acid ester | — | — | D | — | — | D | — |
| Propylene glycol fatty acid ester | — | — | D | — | — | D | — |

<Result>

The compositions of the present invention using as an active ingredient an ester of polyglycerin obtained by polymerizing 3 to 10 glycerins and a fatty acid having 8 to 10 carbon atoms caused a high mortality of the sweet potato whiteflies in comparison with compositions using as an active ingredient a fatty acid ester of monoglycerin or diglycerin, and compositions using as an active ingredient an ester of glycerin and a fatty acid having 12 to 18 carbon atoms.

Moreover, the compositions of the present invention caused a high mortality of the two-spotted spider mites in comparison with compositions using as an active ingredient a compound other than the glycerin fatty acid ester (monoglycerin diaceto monofatty acid ester, glycerin citric and fatty acid ester, sorbitan fatty acid ester, propylene glycol fatty acid ester).

Example 5

Using test chemicals each containing an active ingredient or test chemicals each containing an active ingredient and an auxiliary agent shown in Table 9 below, the control effects against two-spotted spider mite, Kanzawa spider mite, green peach aphid, and sweet potato whitefly were examined by the same methods as those in Examples 1 to 4.

Moreover, as a comparative material, used was a commercially-available insecticididal and microbiocidal agent SUNCRYSTAL emulsion (active ingredient: decanoyloctanoylglycerol (diglycerin, C10 and C8)) (concentration after dilution with water: 200 mg/dl).

Control value=100−((the number of pests alive in a tested plot after the treatment/the number of pests alive in the tested plot before the treatment)/(the number of pests alive in an untreated plot before the treatment/the number of pests alive in the untreated plot after the treatment))×100

Table 9 shows the result.

TABLE 9

|  |  | Control value | | | |
|---|---|---|---|---|---|
| Active ingredient | Auxiliary agent | two-spotted spider mite | Kanzawa spider mite | green peach aphid | sweet potato whitefly |
| triglycerin (C10, esterification degree: 40%) | none | 85 | 98 |  | 98 |
| triglycerin (C10, esterification degree: 50%) | none | 92 | 99 |  |  |

TABLE 9-continued

| Active ingredient | Auxiliary agent | Control value - two-spotted spider mite | Kanzawa spider mite | green peach aphid | sweet potato whitefly |
|---|---|---|---|---|---|
| triglycerin (C10, esterification degree: 40%) | 7643 (1 mass %) | 100 | 92 | 100 | 95 |
| triglycerin (C10, esterification degree: 50%) | 7643 (1 mass %) | 99 | 95 | 98 | |
| SUNCRYSTAL emulsion (200 mg/dl) | none | 54 | 61 | | |

Table 9 shows the control values of the tested chemicals.

In Table 9, for example, triglycerin (C10, esterification degree: 40%) means an ester of a fatty acid having 10 carbon atoms and triglycerin (esterification degree: approximately 40%).

In addition, "7643" means polyoxyethylene cocoamine (product name: SORPOL 7643 (manufactured by TOHO CHEMICAL INDUSTRY Co., Ltd.)).

Example 6

Using test chemicals each containing an active ingredient or test chemicals each containing an active ingredient and an auxiliary agent shown in Table 10 below, the control effects against two-spotted spider mite, Kanzawa spider mite, green peach aphid, and sweet potato whitefly were examined by the same methods as those in Examples 1 to 4.

Moreover, as a comparative material, used was a commercially-available insecticididal and microbiocidal agent SUNCRYSTAL emulsion (active ingredient: decanoyloctanoylglycerol (diglycerin, C10 and C8)) (concentration after dilution with water: 125 mg/dL).

Control value=100−((the number of pests alive in a tested plot after the treatment/the number of pests alive in the tested plot before the treatment)/(the number of pests alive in an untreated plot before the treatment/the number of pests alive in the untreated plot after the treatment))×100

Table 10 shows the result.

TABLE 10

| Active ingredient | Auxiliary agent | Control value - two-spotted spider mite | Kanzawa spider mite | green peach aphid | sweet potato whitefly |
|---|---|---|---|---|---|
| triglycerin (C8, esterification degree: 30%) | none | 90 | 87 | 97 | |
| triglycerin (C8, esterification degree: 40%) | none | 93 | 83 | | |
| triglycerin (C8, esterification degree: 50%) | none | 89 | 87 | | |
| triglycerin (C10, esterification degree: 30%) | none | 91 | 91 | 100 | |
| triglycerin (C10, esterification degree: 40%) | none | 90 | 97 | 98 | |
| triglycerin (C10, esterification degree: 50%) | none | 94 | 92 | 98 | |
| triglycerin (C8, esterification degree: 30%) | 7643 (1 mass %) | | 86 | | |
| triglycerin (C8, esterification degree: 40%) | 7643 (1 mass %) | | 98 | | |
| triglycerin (C8, esterification degree: 50%) | 7643 (1 mass %) | | 91 | | |
| triglycerin (C10, esterification degree: 30%) | 7643 (1 mass %) | | 91 | | |
| triglycerin (C10, esterification degree: 40%) | 7643 (1 mass %) | 95 | 97 | 91 | 94 |
| triglycerin (C10, esterification degree: 50%) | 7643 (1 mass %) | 99 | 95 | 94 | |
| SUNCRYSTAL emulsion (125 mg/dl) | none | | 64 | | |

Table 10 shows the control values of the tested chemicals.

In Table 10, for example, triglycerin (C8, esterification degree: 30%) means an ester of a fatty acid having 8 carbon atoms and triglycerin (esterification degree: approximately 30%).

In addition, "7643" means polyoxyethylene cocoamine (product name: SORPOL 7643 (manufactured by TOHO CHEMICAL INDUSTRY Co., Ltd.)).

Results of Examples 5 and 6

As can be seen from Tables 9 and 10, the control agents of the present invention had high control actions against two-spotted spider mite, Kanzawa spider mite, green peach aphid, and sweet potato whitefly in comparison with the conventional insecticidal and miticidal agent SUNCRYSTAL emulsion.

Examples 7 to 16

In Examples 7 to 16, using 0.5 g of each active ingredient (a polyglycerin fatty acid ester constituted of one fatty acid and tetraglycerin, esterification degree: 50%) shown in Table 11 having been diluted 500-fold with 100 ml of water (concentration: 500 mg/dL), the control effect against each pest and disease was examined.

Example 7

Effect Against Two-Spotted Spider Mite

Primary leaves of pot-planted kidney bean leaves (variety: Taishoukintokisasage) were inoculated with approximately 200 two-spotted spider mites per leaf.

Two days after the inoculation, the number of the adults on the kidney bean leaves was counted before a treatment. A chemical solution having been adjusted to a predetermined concentration by dilution (0.2 g/100 ml) was sprayed thereon in a sufficient amount.

The plants were left standing in a greenhouse, and the number of the adults was counted 12 days after the treatment to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))×100

Table 11 shows the result.

<Effect Against Kanzawa Spider Mite>

Primary leaves of pot-planted kidney bean leaves (variety: Taishoukintokisasage) were inoculated with approximately 200 Kanzawa spider mites per leaf.

Two days after the inoculation, the number of the adults on the kidney bean leaves was counted before a treatment. A chemical solution having been adjusted to a predetermined concentration by dilution (0.2 g/100 ml) was sprayed thereon in a sufficient amount.

The plants were left standing in a greenhouse, and the number of the adults was counted 12 days after the treatment to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))×100

Table 11 shows the result.

Example 8

Effect Against Broad Mite

New leaves of eggplant (variety: Senryounigou) having been confirmed to be parasitized by broad mites were sprayed with a sufficient amount of a chemical solution having been adjusted to a predetermined concentration by dilution (0.2 g/100 ml).

Fourteen days after the treatment, the effect was determined based on the degree of the treated leaves spread and the degree of new leaf formation, according to the following evaluation criteria.

Evaluation Criteria:
A: recovered
B: slightly recovered
C: not recovered

Table 11 shows the result.

Example 9

Effect Against Tomato Russet Mite

The number of tomato russet mites on tomato leaflets parasitized by the russet mites was examined.

A chemical solution having been adjusted to a predetermined concentration by dilution (0.2 g/100 ml) was sprayed thereon in a sufficient amount.

The plants were placed under a room temperature condition for 5 days, and the number of the individuals alive was examined to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))×100

Table 11 shows the result.

Example 10

Effect Against Western Flower Thrip

Into a perforated plastic container (Munger cell: inner diameter of 20×20×10 mm), 10 to 15 adult western flower *thrips* were put.

The container was left standing at room temperature for several hours, and a chemical solution having been adjusted to a predetermined concentration by dilution (0.2 g/100 ml) was sprayed thereon in a sufficient amount.

Two days after the treatment, the number of the individuals alive was examined to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))×100

Table 11 shows the result.

Example 11

Effect Against Green Peach Aphid

The number of green peach aphids parasitizing white radish leaves (variety: Isabelle) was counted. A sufficient amount of a chemical solution having been adjusted to a predetermined concentration by dilution (0.2 g/100 ml) was sprayed on the white radish leaves parasitized by the green peach aphids.

The treated white radish leaves were placed on healthy white radish leaves, and left standing in a greenhouse for 4 days.

The number of the individuals moved to the healthy white radish leaves was counted to calculate a density index.

Density index=(the number of pests in a tested plot after the treatment/the number of pests in an untreated plot after the treatment)×100

Table 11 shows the result.

Example 12

Effect against Sweet Potato Whitefly

Approximately 200 adult whiteflies per leaf were released to cabbage (variety: Shikidori), and allowed to lay eggs for 2 days. Then, the adults were removed.

The plants were left standing in a greenhouse for 10 days, and the number of the early nymphs was counted.

A chemical solution having been adjusted to a predetermined concentration by dilution (0.2 g/100 ml) was sprayed thereon in a sufficient amount.

The plants were placed in the greenhouse for another 10 days, and the number of the individuals alive was examined to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))× 100

Table 11 shows the result.

Example 13

Effect Against *Camellia* Spiny Whitefly

The number of whitefly early nymphs parasitizing *Camellia sasanqua* was counted.

A chemical solution having been adjusted to a predetermined concentration by dilution (0.2 g/100 ml) was sprayed thereon in a sufficient amount.

The plants were placed at room temperature for 7 days, and the number of the individuals alive was examined to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))× 100

Table 11 shows the result.

Example 14

Effect Against Brown Soft Scale

Into a perforated plastic container (Munger cell: inner diameter of 20×20×10 mm), 10 to 15 early nymphs of brown soft scales were put.

The container was left standing at room temperature for several hours, and a chemical solution having been adjusted to a predetermined concentration by dilution (0.2 g/100 ml) was sprayed thereon in a sufficient amount.

Two days after the treatment, the number of the individuals alive was examined to calculate a control value.

Control value=100−((the number of pests alive in a tested plot after the treatment/the number of pests alive in the tested plot before the treatment)/(the number of pests alive in an untreated plot before the treatment/the number of pests alive in the untreated plot after the treatment))× 100

Table 11 shows the result.

Example 15

Effect Against Gray Mold

Gray mold spores suspended in water ($10^7$ spores/ml) were mixed with a chemical solution having been adjusted to a predetermined concentration by dilution (0.2 g/100 ml).

Flower petals of *Petunia* were inoculated with the mixture, and a ratio of flowers withered two days after the treatment was evaluated based on the following evaluation criteria.

Evaluation Criteria:
1: the ratio of flowers withered=0%
2: the ratio of flowers withered=1 to 20%
3: the ratio of flowers withered=20 to 50%
4: the ratio of flowers withered=50 to 100%

Table 11 shows the result.

Example 16

Effect Against Powdery Mildew

The degree of the disease of pot-planted cucumber leaves (variety: Sagamihanjirofushinari) was examined before a treatment.

A chemical solution having been adjusted to a predetermined concentration by dilution (0.2 g/100 ml) was sprayed thereon in a sufficient amount.

The plants were placed at room temperature for 5 days, and the degree of lesions was evaluated based on the following evaluation criteria.

Evaluation Criteria:
A: no lesions
B: lesions occurred, and the percentage of the area occupied by the lesions to the leaf was less than ¼
C: lesions occurred, and the percentage of the area occupied by the lesions to the leaf was ¼ or higher but less than ½
D: lesions occurred, and the percentage of the area occupied by the lesions to the leaf was ½ or higher Table 11 shows the result.

TABLE 11

| Name of disease/pest | Scientific name | Treatment stage | Effect at dilution ratio of 500 fold | | | |
|---|---|---|---|---|---|---|
| | | | C8 | C10 | C12 | C18 |
| Two-spotted spider mite | *Tetranychus urticae* | egg, nymph, adult | 98 | 100 | 41 | 33 |
| Kanzawa spider mite | *Tetranychus kanzawai* | egg, nymph, adult | 99 | 99 | 48 | 24 |
| broad mite | *Polyphagotarsonemus latus* | egg, nymph, adult | A | A | B | B |
| tomato russet mite | *Aculops lycopersici* | egg, nymph, adult | 100 | 100 | 50 | 0 |
| western flower thrip | *Frankliniella occidentalis* | adult | 85 | 100 | 70 | 20 |
| Green peach aphid | *Myzus persicae* | nymph, adult | 93 | 96 | 85 | 22 |

TABLE 11-continued

| Name of disease/pest | Scientific name | Treatment stage | Effect at dilution ratio of 500 fold | | | |
|---|---|---|---|---|---|---|
| | | | C8 | C10 | C12 | C18 |
| sweet potato whitefly | Bemisia tabaci | early nymph | 89 | 91 | 44 | 9 |
| camellia spiny whitefly | Aleurocanthus camelliae | early nymph | 88 | 94 | 72 | 0 |
| brown soft scale | Coccus hesperidum | early nymph | 73 | 95 | 50 | 2 |
| gray mold | Botrytis cinerea | spore-chemical solution mixing treatment | 1 | 1 | 2 | 3 |
| powdery mildew | Sphaerotheca cucurbitae | when a small lesions occurred | A | A | D | D |

<Result>

As can be seen from Table 11, the control agents of the present invention exhibited remarkable control actions against various plant pests and plant diseases in comparison with conventional control agents containing as an active ingredient a polyglycerin fatty acid ester of a fatty acid having 12 to 18 carbon atoms as a constitutive fatty acid.

Example 17

A polyglycerin fatty acid ester and phosphoric acid were weighed using an electronic balance and put into a cylindrical plastic container (diameter of 27 m×height of 77 mm, volume 25 ml) in such a manner that the mixing ratio was 90:10 (mass ratio) (10 mass % of phosphoric acid (approximately 11.1 parts by mass of phosphoric acid per 100 parts by mass of the polyglycerin fatty acid) was added) or 99.9:0.1 (mass ratio) (0.1 mass % of phosphoric acid (approximately 0.1 parts by mass of phosphoric acid per 100 parts by mass of the polyglycerin fatty acid) was added). The total amount was adjusted to 20 ml. Then, the preparation was made uniform by sufficient stirring and mixing. The resultant was left standing in a cool dark place. Two months later, the degree of aggregation and precipitation of the polyglycerin fatty acid ester was visually determined based on the following determination criteria.

Moreover, a test was conducted by the same method as above using acetic acid, lactic acid, ethyl alcohol, or normal hexane in place of phosphoric acid.

Further, as a reference, a test was conducted by the same method as above using only a polyglycerin fatty acid ester to which no oxoacid or organic solvent was added.

<Determination Criteria>

Index 1: equivalent aggregation and precipitation to those of the reference were observed.

Index 2: the aggregation and precipitation were approximately ¾ of those of the reference.

Index 3: the aggregation and precipitation were approximately ½ of those of the reference.

Index 4: the aggregation and precipitation were approximately ¼ of those of the reference.

Index 5: no aggregate and precipitate were observed.

Table 12 shows the result.

TABLE 12

| Oxoacid or organic solvent | Adding ratio (%) | Result (index) |
|---|---|---|
| phosphoric acid | 10.0 | 5 |
| phosphoric acid | 0.1 | 4 |
| acetic acid | 10.0 | 5 |
| acetic acid | 0.1 | 4 |
| lactic acid | 10.0 | 5 |
| lactic acid | 0.1 | 4 |
| ethyl alcohol | 10.0 | 4 |
| ethyl alcohol | 0.1 | 4 |
| normal hexane | 10.0 | 4 |
| normal hexane | 0.1 | 3 |
| none (reference) | — | 1 |

<Test Result>

Adding an oxoacid or an organic solvent to the polyglycerin fatty acid ester reduced the aggregation and precipitation of the polyglycerin fatty acid ester in comparison with the polyglycerin fatty acid ester alone.

This description includes the contents as disclosed in the description and/or drawings of Japanese Patent Application No. 2012-227006, based on which the present application claims priority. In addition, all the publications, patent, and patent applications cited herein are incorporated herein by reference in their entirety.

INDUSTRIAL APPLICABILITY

The present invention makes it possible to efficiently control plant pests and/or plant diseases in comparison with conventional control agents. Thus, the control agent and the control method of the present invention are quite industrially useful.

The invention claimed is:

1. A method for controlling a plant pest and/or a plant disease, comprising spraying a plant with a control agent comprising a polyglycerin fatty acid ester as an active ingredient, wherein
   the polyglycerin fatty acid ester is an ester of at least one fatty acid selected from caprylic acid and capric acid and at least one polyglycerin obtained by polymerizing 3 to 10 glycerins, and
   the polyglycerin fatty acid ester has an esterification degree of 20 to 100%.

2. The method according to claim 1, wherein the plant is sprayed with the polyglycerin fatty acid ester at a concentration of 10 mg/dL to 2000 mg/dL.

3. The method according to claim 1, wherein the polyglycerin contains at least one selected from triglycerin, tetraglycerin, and decaglycerin.

4. The method according to claim 1, wherein the plant pest is at least one selected from the group consisting of aphids, whiteflies, mites, *thrips*, and scale insects.

5. The method according to claim 1, wherein the plant disease is at least one selected from the group consisting of gray mold and powdery mildew.

6. The method according to claim 1, wherein the polyglycerin fatty acid ester has an esterification degree of 30 to 80%.

7. The method according to claim 1, further comprising a surfactant.

8. The method according to claim 7, wherein the surfactant includes polyoxyethylene cocoamine.

9. The method according to claim 1, further comprising an organic solvent.

10. The method according to claim 1, further comprising an oxoacid.

11. The method according to claim 1, wherein the polyglycerin fatty acid ester has an esterification degree of 30 to 60%.

12. The method according to claim 9, wherein the organic solvent is selected from the group consisting of acetone, isobutyl alcohol, isopropyl alcohol, isopentyl alcohol, ethyl ether, ethyl alcohol, xylene, cresols, cyclohexane, isobutyl acetate, ethyl acetate, chloroform, normal hexane, normal propyl alcohol and methanol.

13. The method according to claim 10, wherein the oxoacid is selected from the group consisting of boric acid, carboxylic acids, nitric acid, phosphorous acid, phosphoric acid, sulfurous acid, sulfuric acid, acetic acid, propionic acid, butyric acid, valeric acid, lactic acid and sulfonic acids.

* * * * *